(12) United States Patent
Sabesan

(10) Patent No.: US 6,852,866 B2
(45) Date of Patent: Feb. 8, 2005

(54) TRIAZOLE LINKED CARBOHYDRATES

(75) Inventor: Subramaniam Sabesan, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/641,448

(22) Filed: Aug. 15, 2003

(65) Prior Publication Data

US 2004/0059105 A1 Mar. 25, 2004

Related U.S. Application Data

(62) Division of application No. 09/651,712, filed on Aug. 31, 2000, now Pat. No. 6,664,399.
(60) Provisional application No. 60/152,063, filed on Sep. 2, 1999.

(51) Int. Cl.[7] ............................................. C07D 315/00
(52) U.S. Cl. ........................ 549/420; 549/417; 549/419; 549/478; 549/480
(58) Field of Search .................................. 549/420, 478, 549/417, 419, 480

(56) References Cited

U.S. PATENT DOCUMENTS

| | | | | |
|---|---|---|---|---|
| 4,958,037 A | * | 9/1990 | Floyd, Jr. | .................... 549/476 |
| 5,512,470 A | | 4/1996 | Sabesan | |
| 6,130,326 A | | 10/2000 | Ramasamy et al. | |
| 6,664,399 B1 | * | 12/2003 | Sabesan | ........................ 548/256 |
| 2002/0165168 A1 | | 11/2002 | Bunger et al. | |

OTHER PUBLICATIONS

Logue et al, Proceedings N. Dak. Acad. Sci. vol. 34, 6 (1980), abrstract, C–nucleoside synthesis via allkynyl ketones.*

Parsons, J.A. "Peptide Hormones" Jun. 1976, University Park Press, London, 1–6.

Wolfgang Broder and Horst Kunz, Glycosyl Azides as Building Blocks in Convergent Syntheses of Oligomeric Lactosemine and Lewis Saccharides, Bioorganic & Medicinal Chemistry, 5, 1–18, 1997.

Wolfgang Broder and Horst Kunz, A new method of anomeric protection and activation based on the conversion of glycosyl azides into glycosyl glourides, Carbohydrate Research, 249. 221–241, 1993.

Shigeru Mio, YukoKumagawa and Soji Sugai, Synthetic Studies on (+)–Hydantocidin(3); A New Synthetic Method for Construction of the Spiro–Hydantoin Ring at the Anomeric Position of D–Ribofuranose, Tetrahedron, 47. 2133–2144, 1991.

Thomas L. Cupps, Raymond H. Boutin and Henry Rapoport, a–Amino Acids as Chiral Educts for Asymmetric Products. The Synthesis of a '–Amino–a, β–yones. J.Org. Chem, 5D, 3972–3979, 1985.

Csaba Peto, Gyula Batta, Zolta'n Györgydea'k and Ferenc Szlaricskai, Glycoside Synthesis With Anomeric, J.Carbohydrate Chemistry, 15(4), 405–483, 1996.

Fre'deric Louerat, Khalid Bougrin, Andre' Loupy, Ana M. Ochoa de Retana, Jalone Pagalday and Francisco Palacios, Cycloaddition Reactions of Azidomethyl Phosphonate with Acetylenes and Enamines. Synthesis of Triazoles. hETEROCYCLES, 48, 161–170, 1998.

Zoltan Györgydeak, Laszio Szilagyi and Hans Paulsen, Synthesis, Structure and Reactions of Glycosyl Azides, J. Carbohydrate Chemistry, 12(2), 139–163, 1993.

(List continued on next page.)

Primary Examiner—Cecilia J. Tsang
Assistant Examiner—Raymond Covington

(57) ABSTRACT

Disclosed is an invention concerning triazolyl-oligosaccharides, oligosaccharides wherein the bonding between the saccharide groups is via a triazole group and methods for their preparation.

5 Claims, 6 Drawing Sheets

OTHER PUBLICATIONS

Subramaniam Sabesan, et al, Cluster Siatoside Inhibitors for Influenza Virus: Synthesis, NMR, and Biological Studies. American Chemical Society, (1992), pp. 8363–8375, vol. 114, Wilmington, DE.

K.C. Nicolaou, et al. Handbook of Combinatorial Chemistry, Chemical Synthesis of Oligosaccharides, pp. 704–722, vol. 2, Germany.

* cited by examiner

TRIAZOLE LINKED CARBOHYDRATES

This application is a division of application Ser. No. 09/651,712, filed Aug. 31, 2000, now U.S. Pat. No. 6,664,399, (which is incorporated in its entirety as a part hereof for all purposes), which claimed the benefit of U.S. Provisional Application No. 60/152,063, filed Sep. 2, 1999.

FIELD OF THE INVENTION

This invention concerns triazolyloligosaccharides, compounds having more than one oligosaccharide wherein the bonding between the oligosaccharide groups is a triazole group. Further disclosed is a process for the preparation of these triazolyloligosaccharides, the use of the compounds as potential enzyme inhibitors, and acetylenic intermediate compounds.

TECHNICAL BACKGROUND OF THE INVENTION

Host cell surface oligosaccharides serve as receptor ligands for protein molecules such as enzymes, antibodies and lectins, and they initiate many critical biological reactions. Unfortunately, these receptor ligands also initiate many harmful biological reactions by providing attachment sites for viruses, toxins, bacteria, etc.

Normally in an oligosaccharide, the constituent monosaccharide groups are linked by ether oxygen linkages. This ether oxygen linkage is difficult to construct chemically. Linking methods are specific for each sugar employed. The ether oxygen linking group is susceptible to hydrolysis by glycosyl hydrolases and non-enzymatic chemical hydrolysis. This ease of hydrolysis makes it difficult to use carbohydrate structures as pharmaceuticals. Further, there are no known methods of automated syntheses for complex oxygen ether linked carbohydrates.

The present invention provides saccharide compounds wherein the linkage is less susceptible to hydrolysis and methods for their preparation.

SUMMARY OF THE INVENTION

This invention provides a compound having the structure I,

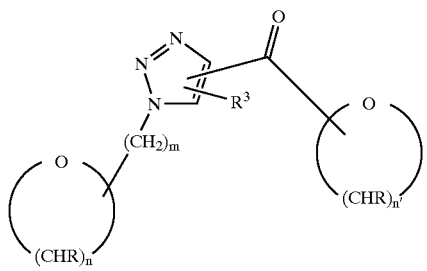

I wherein each R, independently, is selected from the group consisting of hydrogen, hydroxy, alkoxy having up to 8 carbon atoms, acyloxy having up to 8 carbon atoms, acylamino having up to 8 carbon atoms, $C_1$ to $C_{20}$ hydrocarbyl and substituted hydrocarbyl and amino;

$R^3$ is selected from the group consisting of H, $C_1$ to $C_{20}$ hydrocarbyl and substituted hydrocarbyl;

m is 0 or 1, and n and n' are, independently, 4 or 5.

Also provided are compounds containing three or more rings characterized in that the linkage between the several rings is a triazolyl group-containing moiety of the structure

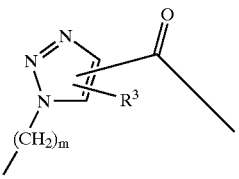

where m and $R^3$ are defined as above.

This invention provides a compound of the structure II, wherein $R^1$ is selected from the group consisting of H, Na, $C_1$–$C_{20}$ alkyl, wherein $R^2$ is selected from the group consisting of hydroxy, alkoxy having from 1 to 8 carbon atoms, acyloxy having from 1 to 8 carbon atoms, acylamino having

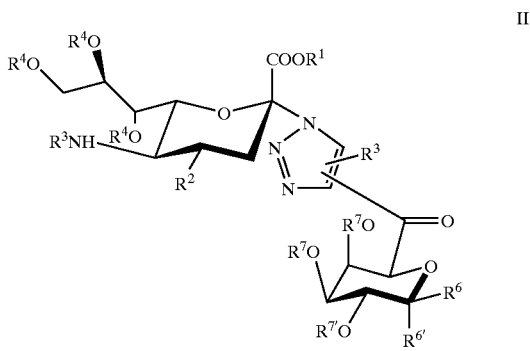

II from 1 to 8 carbon atoms, amino, hydrogen, and guanidino;

wherein $R^3$ is selected from the group consisting of H, $C_1$ to $C_{20}$ hydrocarbyl, and substituted hydrocarbyl;

wherein $R^4$ is selected from the group consisting of H, acyl having from 1 to 8 carbon atoms, and alkyl having 1 to 20 carbon atoms;

wherein $R^6$ and $R^{6'}$ are selected from the group consisting of H, OH, $C_1$ to $C_{20}$ alkoxy, $C_1$ to $C_{20}$ substituted alkoxy, mono-, di- or oligosaccharide, and alkylideneoxy taken together with $R^{7'}$ when $R^{7'}$ is not H, provided that one of $R^6$ and $R^{6'}$ must be H but $R^6$ and $R^{6'}$ may not both be H; and $R^7$ and $R^{7'}$ are selected from the group consisting of H, acyl having from 1 to 8 carbon atoms, $C_1$ to $C_{20}$ alkyl, aryl, and alkylidene taken together with an adjacent $R^6$, $R^{6'}$, $R^7$ or $R^{7'}$.

Also provided are a compound of the structure III, wherein $R^3$ is selected from the group consisting of H, $C_1$ to $C_{20}$ hydrocarbyl, and $C_1$ to $C_{20}$ substituted hydrocarbyl; $R^8$ is selected from the group consisting of H, alkyl having from 1 to 20 carbon atoms, and acyl having from 1 to 8 carbon atoms;

III

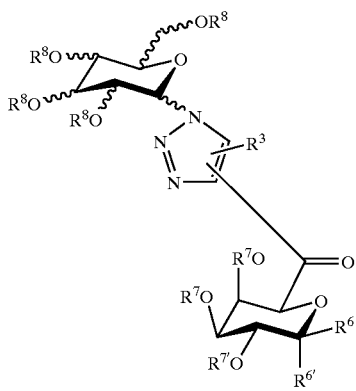

wherein $R^6$ and $R^{6'}$ are selected from the group consisting of H, OH, $C_1$ to $C_{20}$ alkoxy, $C_1$ to $C_{20}$ substituted alkoxy, mono-, di- or oligosaccharide, and alkylideneoxy taken together with $R^{7'}$, when $R^{7'}$ is not H, provided that one of $R^6$ and $R^{6'}$ must be H but $R^6$ and $R^{6'}$ may not both be H; and wherein $R^7$ and $R^{7'}$ are selected from the group consisting of H, acyl having from 1 to 8 carbon atoms, $C_1$ to $C_{20}$ alkyl, aryl, and alkylidene taken together with an adjacent $R^6$, $R^{6'}$, $R^7$ or $R^{7'}$.

Also disclosed is a process for the preparation of a compound having the structure I, comprising: contacting azides of the structure IA:

IA

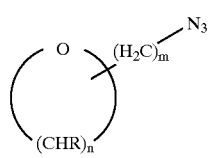

wherein R is selected from the group consisting of hydrogen, hydroxy, alkoxy having up to 8 carbon atoms, acyloxy having up to 8 carbon atoms, acylamino having up to 8 carbon atoms, $C_1$ to $C_{20}$ hydrocarbyl or substituted hydrocarbyl and amino; n and n' are, independently, 4 or 5, and m is 0 or 1, with compounds of the structure IB

IB

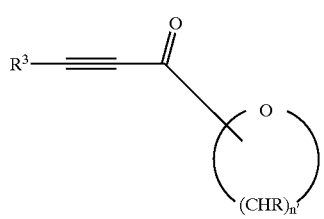

wherein R is as described above and $R^3$ is selected from the group consisting of H, $C_1$ to $C_{20}$ hydrocarbyl and substituted hydrocarbyl.

The present invention also discloses a process for the preparation of a combinatorial library of compounds of the structure I, comprising contacting one or more azides of the structure IA:

IA

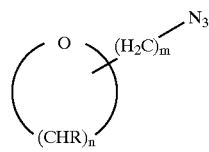

wherein R is selected from the group consisting of hydrogen, hydroxy, alkoxy having up to 8 carbon atoms, acyloxy having up to 8 carbon atoms, acylamino having up to 8 carbon atoms, $C_1$ to $C_{20}$ hydrocarbyl and substituted hydrocarbyl and amino; n and n' are, independently, 4 or 5, and m is 0 or 1, with one or more compounds of the structure IB

IB wherein R is as described above and $R^3$ is selected from the group consisting of H, $C_1$ to $C_{20}$ hydrocarbyl and substituted hydrocarbyl.

This invention is also directed to the compounds of Formula IB and Formula IIB.

DETAILED DESCRIPTION OF THE INVENTION

Figure 1:
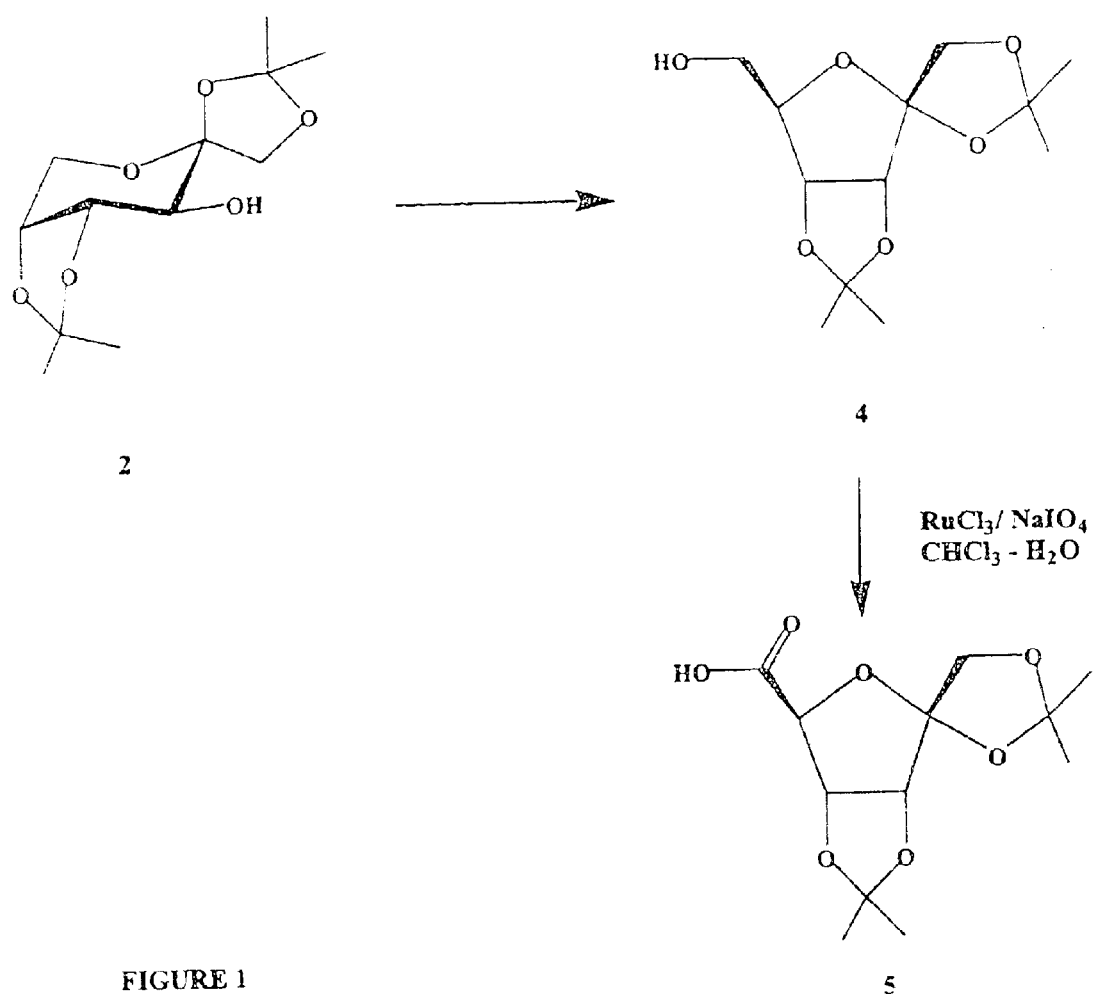
FIG. 1 is a representation of the synthetic route to starting material compound 5.

The compounds of the present invention are di- or polysaccharides where the link between at least two of the carbohydrate groups is via a 1,2,3-triazole group where the N-1 nitrogen atom of the triazole ring is linked to a first saccharide group, optionally, to the anomeric carbon atom of that sugar.

The 4-carbon atom or the 5-carbon atom of the triazole ring is bound to a second saccharide group via a carbonyl group. This carbonyl group may be attached to the second saccharide group at any carbon atom, but is preferably bound to the 6-carbon atom of a six carbon atom saccharide group.

The compounds can be further functionalized to enlarge the family.

The compounds of the present invention are expected to be synthesized by more general methods than ether oxygen-linked carbohydrates, are expected to be more stable to enzymatic and chemical hydrolysis and are expected to be amenable to automated synthesis methods. A variety of mimics of natural and unnatural carbohydrates can be made by this method. They may find utility as enzyme inhibitor antiviral agents and, potentially, as pharmaceuticals. Because of the wide variety of substituents that may be placed on the carbohydrate groups, the compounds are capable of extension to "libraries" of compounds by the tecniques commonly used in combinatorial chemistry.

Also provided herein is a process for preparing the compounds of the structure I as shown in Equation 1, below. In a particularized form, the compound of Formula IB may take the form of the compound of Formula IIB:

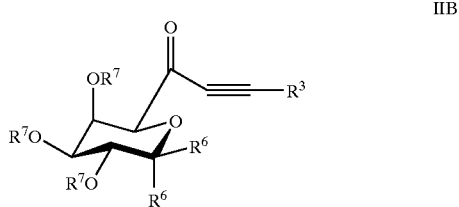

IIB wherein $R^3$ is selected from the group consisting of H, $C_1$ to $C_{20}$ hydrocarbyl and substituted hydrocarbyl;

$R^6$ and $R^{6'}$ are selected from the group consisting of H, OH, $C_1$ to $C_{20}$ alkoxy and substituted alkoxy, mono-, di- or oligosaccharide, and alkylideneoxy taken together with $R^{7'}$ when $R^{7'}$ is not H, provided that one of $R^6$ and $R^{6'}$ must be H but $R^6$ and $R^{6'}$ may not both be H; and $R^7$ and $R^{7'}$ are selected from the group consisting of H, acyl having from 1 to 8 carbon atoms, $C_1$ to $C_{20}$ alkyl, aryl, and alkylidene taken together with an adjacent $R^6$, $R^{6'}$, $R^7$ or $R^{7'}$.

The route originates from azido compounds, which are in turn prepared from phosphate precursors or from chloro or bromo or the corresponding hydroxy compounds. U.S. Pat. No. 5,288,859, incorporated by reference, provides a process for the stereospecific preparation of glycosyl azides (the azido group residing at the anomeric carbon atom) by reacting a metal azide with a glycosyl phosphate triester. U.S. Pat. No. 5,095,123, incorporated by reference, provides a process for the glycosyl phosphate triester compounds.

EQUATION 1

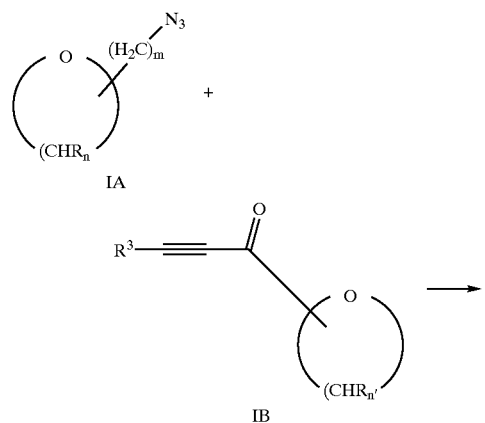

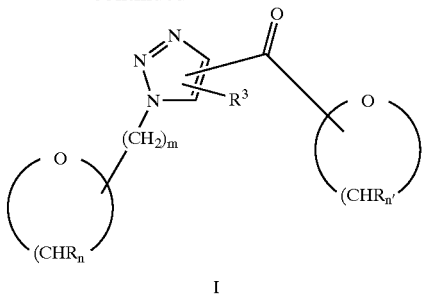

I

The processes disclosed herein are also useful for the preparation of triazole link containing oligomers and polymers by selection of the appropriate difunctional precursors, i.e., carbohydrates containing both acetylenic acid groups and azido groups or carbohydrates containing two azides groups or two acetylenic groups.

Compounds of the present invention are useful as potential inhibitors of glycosidase activity, and/or are expected to be resistant to glycosidase hydrolysis activity.

Preferred compounds of the structures I, II, and III are those where the second saccharide group is bound to the 4-carbon atom of the triazole ring, wherein $R^3$ at the 5-carbon atom of the triazole ring is hydrogen and wherein m (in structure I) is 0; i. e. compounds of the structures IV, V, and VI below:

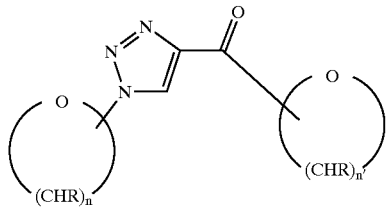

IV where each R, independently, is selected from the group consisting of hydrogen, hydroxy, alkoxy containing up to 8 carbon atoms, acyloxy containing up to 8 carbon atoms, acylamino containing up to 8 carbon atoms, $C_1$ to $C_{20}$ hydrocarbyl or substituted hydrocarbyl and amino; and n and n' are, independently, 4 or 5;

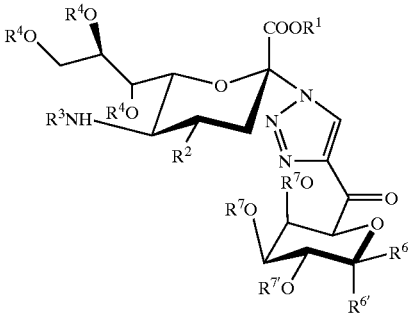

V wherein
$R^1$ is H, Na, or $C_1$–$C_{20}$ alkyl,
$R^2$ is hydroxy, alkoxy containing from 1 to 8 carbon atoms, acyloxy containing from 1 to 8 carbon atoms, acylamino containing from 1 to 8 carbon atoms, amino, hydrogen, or guanidino;

$R^3$ is H or a $C_1$ to $C_{20}$ hydrocarbyl or substituted hydrocarbyl;

$R^4$ is H, acyl containing from 1 to 8 carbon atoms or alkyl containing 1 to 20 carbon atoms;

$R^6$ and $R^{6'}$ are H, OH, a $C_1$ to $C_{20}$ alkoxy or substituted alkoxy, a mono-, di- or oligosaccharide, or an alkylideneoxy taken together with $R^{7'}$ when $R^{7'}$ is not H, provided that one of $R^6$ and $R^{6'}$ must be H but $R^6$ and $R^{6'}$ may not both be H; and $R^7$ and $R^{7'}$ are H, acyl containing from 1 to 8 carbon atoms, or a $C_1$ to $C_{20}$ alkyl, aryl, or alkylidene taken together with an adjacent $R^6$, $R^{6'}$, $R^7$ or $R^{7'}$;

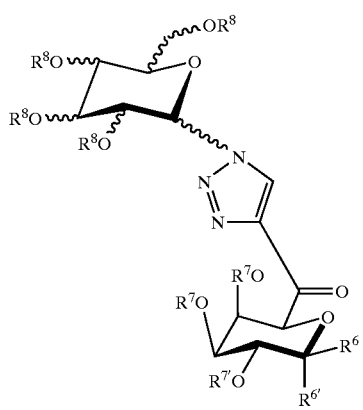

VI wherein $R^3$ is H or a $C_1$ to $C_{20}$ hydrocarbyl or substituted hydrocarbyl;

$R^8$ is H, alkyl, where the alkyl contains from 1 to 20 carbon atoms, or acyl, where the acyl group contains from 1 to 8 carbon atoms;

$R^6$ and $R^{6'}$ are H, OH, a $C_1$ to $C_{20}$ alkoxy or substituted alkoxy, a mono-, di- or oligosaccharide, or an alkylideneoxy taken together with $R^{7'}$ when $R^{7'}$ is not H, provided that one of $R^6$ and $R^{6'}$ must be H but $R^6$ and $R^{6'}$ may not both be H; and $R^7$ and $R^{7'}$ are H, acyl containing from 1 to 8 carbon atoms, or a $C_1$ to $C_{20}$ alkyl, aryl, or alkylidene taken together with an adjacent $R^6$, $R^{6'}$, $R^7$ or $R^{7'}$.

EXAMPLES

The following examples illustrate the process of the present invention, but are not intended to limit it in any manner. All the reagents were purchased from Aldrich Chemical Co., Milwaukee, Wis. Thin layer chromatography of the reaction mixture to monitor the progress of the reaction was performed on precoated plates of Silica Gel 60 F.sub.254 (EM Science, Gibbstown, N.J.), and the spots were visualized with a spray containing 5% sulfuric acid in ethanol followed by heating. Column chromatography was done on silica gel 60 (230–400 mesh, EM Science). $^1$H NMR spectra were recorded at 400 MHz (Bruker instrument). The hydrogen chemical shifts in deuterated chloroform, $CDCl_3$, are expressed relative to tetramethylsilane.

Isolation of the desired product is achieved by means common in the art. For example, the desired product can be isolated by high pressure liquid chromatography or column chromatography. Exemplary details are provided hereinafter in the examples.

Preparation of Starting Materials 1,2,3,4-Di-O-isopropylidene-D-psicofuranose uronic acid (5)

Reaction Scheme in FIG. 1

Compound 5 was prepared by the oxidation of 4, which was made from D-fructose (1), via compound 2, according to the literature procedure (S. Mio, Y. Kumagawa and S. Sugai, *Tetrahedron* (1991), 47, 2133–2144).

Compound 4 (32.4 g) was dissolved in a mixture of $CHCl_3$—water (1:1, 480 ml) containing sodium periodate (94 g), benzyltriethylammonium chloride (1.4 g) and stirred vigorously by a mechanical stirrer. Ruthenium(III)chloride (540 mg) was dissolved in minimum volume of water and added slowly to the above mixture. After the addition was over, the reaction mixture was refluxed under stirring for 2 h, coooled, the insoluble material filtered and the filtrate was washed with water. Subsequently, saturated sodium sulfite solution was added till the aqueous layer became basic to enable the product dissolve in the aqueous layer. The organic layer was then removed and the aqueous layer was washed once again with methylene chloride. The aqueous layer was then rendered acidic with ice cold hydrochloric acid and the product was extracted with extracted with methylene chloride and washed with water and saturated sodium chloride solution. After drying, the organic layer was concentrated to dryness to obtain the product a colorless solid (26.6 g). $^1$H-NMR ($CDCl_3$): 5.16 (dd, J=0.9, 5.7 Hz, H-4), 4.67 (broad s, H-5), 4.63 (d, J=5.7 Hz, H-3), 4.40 (d, J=10.4 Hz, H-1a), 4.18 (d, J=10.4 Hz, H-1b), 1.57, 1.46, 1.42, and 1.34 (4×s, isopropylidene methyls).

2,3,4,5-Di-O-isopropylidene-D-arabino-hexulopyranosylonic acid (7)

Figure 2:
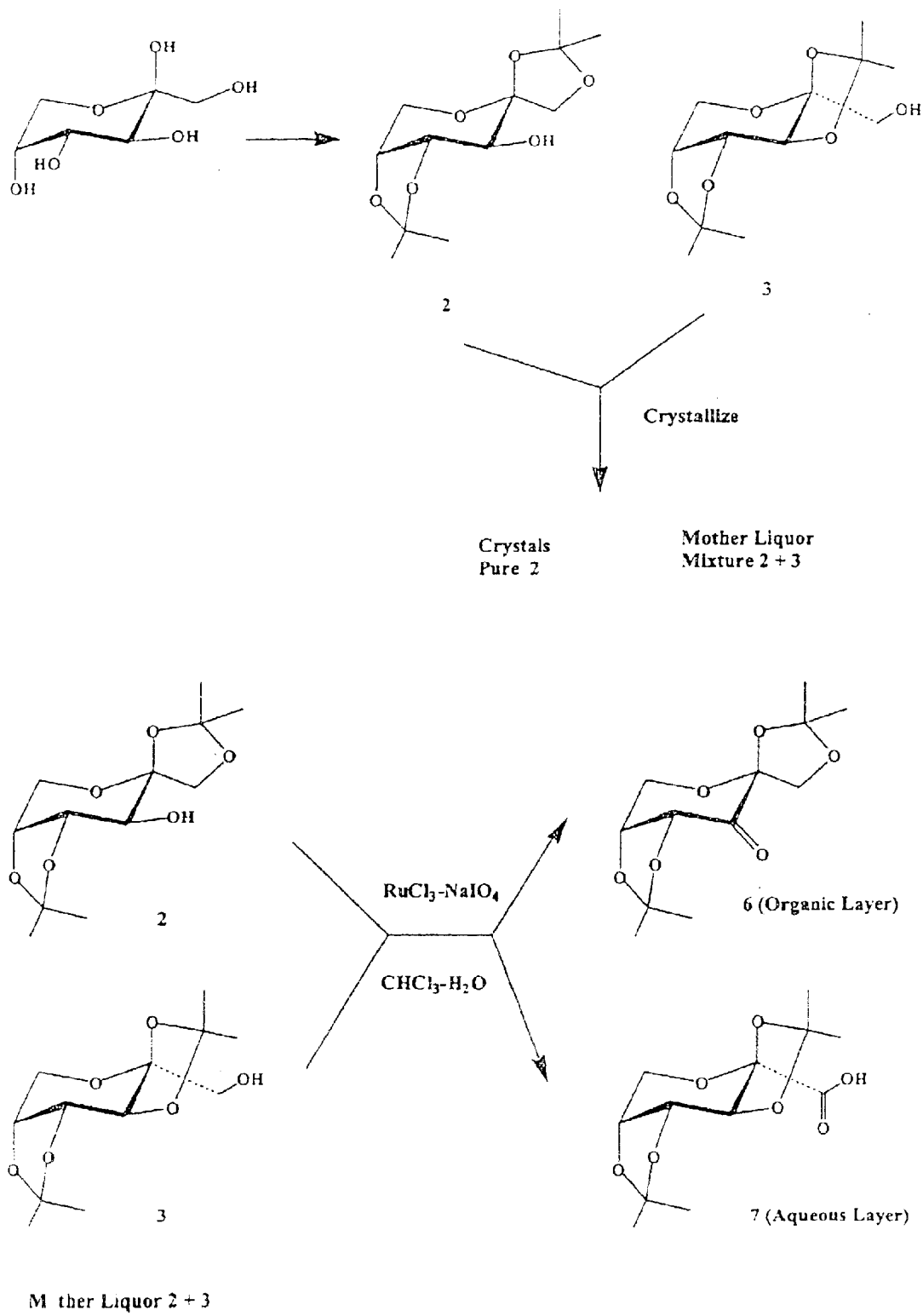
FIG. 2 is a representation of the synthetic route to intermediate compounds 6 and 7.

Reaction Scheme in FIG. 2

D-Fructose (1) (75.0 g) was reacted with 2,2-dimethoxypropane (30.1 ml) and perchloric acid (17.5 ml) in acetone (1.5 l) according to the literature procedure (S. Mio, Y. Kumagawa and S. Sugai, *Tetrahedron* (1991), 47, 2133–2144). The crude product (78.0 g) when recrystallized from methylene chloride-hexane gave pure 2 (22 g) and the mother liquor contained a mixture of 2 and 3 (56 g).

The mixture of 2 and 3 (56.0 g) was oxidized with sodium periodate (150 g) and $RuCl_3$ (1.6 g) in presence of benzyltrietylammonium chloride (1.7 g) and potassium carbonate (10.0 g) in chloroform-water (1:1, 950 ml) as described above for 5. The excess oxidants were neutralized with 2-propanol (100 ml) and the reaction mixture was processed as described above. The desired carboxylic acid 7 remained in the aqueous sodium sulfite layer, while the ketone 6 remained in the organic layer. Acidification of the aqueous layer with ice cold HCl followed by extraction with methylene chloride afforded pure 7 (27 g). $^1$H-NMR ($CDCl_3$): 4.65 (m, H-3 and H-5), 4.28 (broad d, J=7.6 Hz, H-4), 3.98 (dd, J=1.9, 12.9 Hz, H-6a), 3.93 (broad d, J=12.9 Hz, H-6b), 1.58, 1.54, 1.47, and 1.36 (4×s, isopropylidene methyls).

1,2,3,4-Di-O-isopropylidene-D-galactopyranose uronic acid 8 Compound 8 was Prepared as Described in the Literature(S. Sabesan, U.S. Pat. No. 5,756,712 (1998) Incorporated Herein by Reference). N-Methoxy-N-methyl(1,2,3,4-Di-O-isopropylidene-D-psicofuranose aronic acid)amide 9

Figure 3:
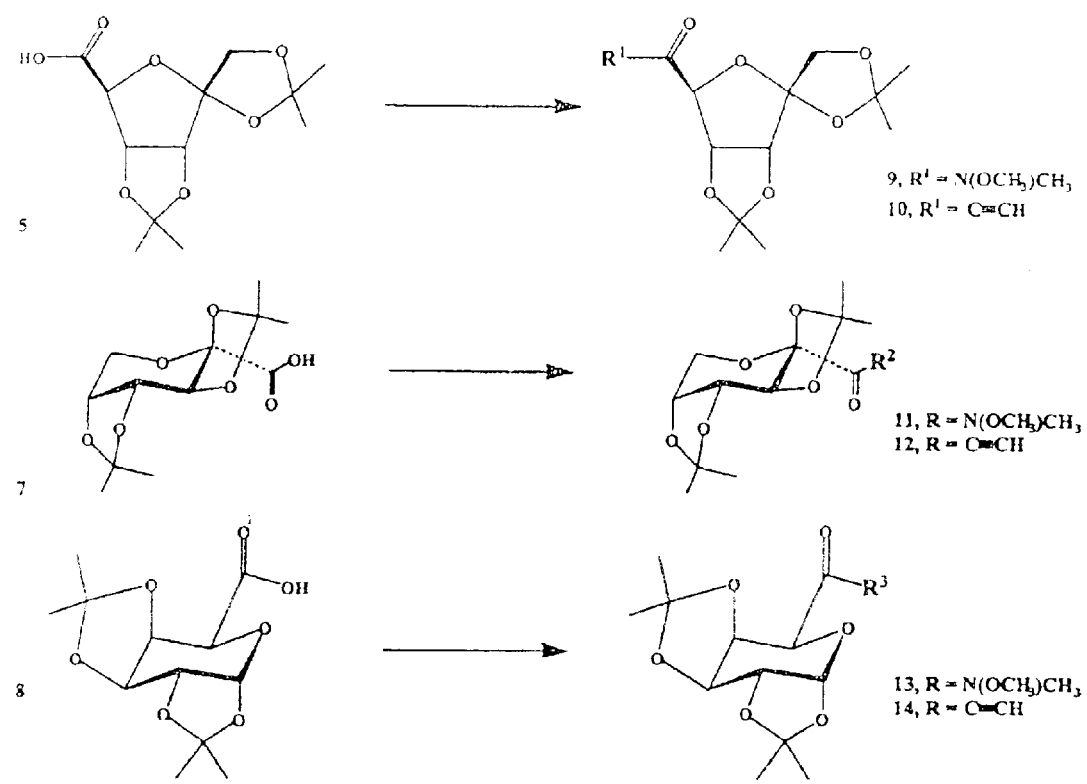
FIG. 3 is a representation of the synthetic routes to intermediate eynone compounds 10, 12 and 14.

Reaction Shown in FIG. 3

Carboxylic acid 5 (5.15 g, 18.8 mmol) was disssolved in minimum volume of anhydrous acetonitrile. To this a saturated solution of 1,1'-carbonylbis(3-methylimidazolium triflate) {CBMIT 9.21 g, 18.8 mmol, for preparation see, S. Sabesan, U.S. Pat. No. 5,756,712 (1998)} was added and stirred under dry atmosphere for 5 min. It was then added in drops to a solution of N,O-dimethyl-hydroxylamine hydrochloride (2.6 g) and triethylamine (3.0 g) in acetonitrile and stirred for 2 h. After 2 h, saturated aqueous sodium bicarbonate solution (2 ml) was added and the reaction mixture was concentrated to dryness. The reaction product was dissolved in methylene chloride (200 ml) and washed with water, ice cold 0.5 M HCl and saturated aqueous bicarbonate solution. The solution was dried and concentrated to dryness. Weight of the product was 4.3 g. $^1$H-NMR (CDCl$_3$): 5.35 (broad s, H-4), 4.88 (broad s, H-3), 4.71 (d, J=6.0 Hz, H-5), 4.29 (d, J=10.1 Hz, H-1a), 4.08 (d, J=10.4 Hz, H-1b), 3.78 (s, N—OC$\underline{H}_3$), 3.21 (s, N—C$\underline{H}_3$), 1.46, 1.45, 1.37, & 1.34 (4×s, CH$_3$).

N-Methoxy-N-methyl(2,3,4,5-Di-O-isopropylidene-D-arabino-hexulopyranosylonic acid)amide 11

Reaction Shown in FIG. 3

Carboxylic acid 7 (5.15 g, 18.8 mmol) was disssolved in minimum volume of anhydrous acetonitrile. To this a saturated solution of 1,1'-carbonylbis(3-methylimidazolium triflate) {CBMIT 9.20 g, 18.8 mmol, for preparation see, S. Sabesan, U.S. Pat. No. 5,756,712 (1998)} was added and stirred under dry atmosphere for 5 min. It was then added in drops to a solution of N,O-dimethyl-hydroxylamine hydrochloride (2.6 g) and triethylamine (2.8 g) in acetonitrile and stirred for 2 h. After 2 h, saturated aqueous sodium bicarbonate solution (2 ml) was added and the reaction mixture was concentrated to dryness. The reaction product was dissolved in methylene chloride (200 ml) and washed with water, ice cold 0.5 M HCl and saturated aqueous bicarbonate solution. The solution was dried and concentrated to dryness. Weight of the product was 4.7 g. $^1$H-NMR (CDCl$_3$): 5.27 (d, J=2.3 Hz, H-3), 4.64 (dd, J=2.8, 7.6 Hz, H-4), 4.24 (d, J=7.6 Hz, H-5), 3.89 (d, J=12.0 Hz, H-6a), 3.76 (d, J=12.9 Hz, H-6b), 3.72 (N—OC$\underline{H}_3$), 3.36 (broad s, N—C$\underline{H}_3$), 1.53, 1.42, 1.35, 1.34 (4×s, isopropylidene methyls).

N-Methoxy-N-methyl(1,2,3,4-Di-O-isopropylidene-D-galactopyranose aronic acid)amide 13

Reaction Shown in FIG. 3

1,2,3,4-Di-O-isopropylidene-D-galactopyranose uronic acid 8 (5.56 g) was activated with CBMIT (9.2 g) in anhydrous acetonitrile (62 ml) and added to a solution of N,O-dimethylhydroxylamine hydrochloride (2.6 g) and trietylamine (2.6 g) in acetonitrile (25 ml). After 2 h, saturated aqueous sodium bicarbonate solution (2 ml) was added and the reaction mixture was concentrated to dryness. The reaction product was dissolved in methylene chloride (200 ml) and washed with water, ice cold 0.5 M HCl and saturated aqueous bicarbonate solution. The solution was dried and concentrated to dryness. The weight of the crude product was 4.4 g. $^1$H-NMR (CDCl$_3$): 5.63 (d, H-1), 4.71 (broad s, H-5), 4.63 (m, H-3 and H-4), 4.37 (m, H-2), 3.72 (s, N—OC$\underline{H}_3$), 3.24 (s, N—C$\underline{H}_3$), 1.54, 1.48, 1.35 and 1.32 (4×s, isopropylidene methyls).

Preparation of Eynone 10

Structure Shown in FIG. 3

To a solution of the Weinreb amide 9 (2.61 g, 8.2 mmol) in dry THF (20 ml), a solution of ethynyl magnesium bromide (0.5 M, 26.3 ml, 13.15 mmol) in THF was added in drops and stirred at room temperature for 4 h. The reaction mixture was then poured over ice cold 0.5 M aqueous HCl, followed by the addition of methylen chloride (150 ml). The organic layer was separated and washed with water and brine. The product was purified by chromatography on a column of silica gel using ethylacetate-hexane (3:8) as eluant. The weight of the product was 1.64 g. $^1$H-NMR (CDCl$_3$): 5.38 (dd, J=1.1, 6.0 Hz, H-4), 4.52 (d, J=6.0 Hz, H-3), 4.48 (broad s, H-5), 4.35 (d, J=10.2 Hz, H-1a), 4.18 (d, J=10.2 Hz, H-1b), 3.38 (s, C$\underline{H}$), 1.55, 1.45, 1.36, and 1.34 (4×s, isopropylidene methyls).

Preparation of Eynone 12

Structure Shown in FIG. 3

To a solution of the Weinreb amide 11 (3.53 g, 11.1 mmol) in dry THF (20 ml), a solution of ethynyl magnesium bromide (0.5 M, 35.6 ml, 17.8 mmol) in THF was added in drops and stirred at room temperature for 4 h. The reaction mixture was then poured over ice cold 0.5 M aqueous HCl, followed by the addition of methylen chloride (150 ml). The organic layer was separated and washed with water and brine. The product was purified by chromatography on a column of silica gel using ethylacetate-hexane (3:8) as eluant. The weight of the product was 1.80 g. $^1$H-NMR (CDCl$_3$): 4.75 (d, J=2.3 Hz, H-3), 4.62 (dd, J=2.6, 7.9 Hz, H-4), 4.26 (m, H-5), 3.94 (m, H-6a, H-6b), 3.44 (s, C$\underline{H}$), 1.56, 1.44, 1.41, and 1.33 (4×s, isopropylidene methyls).

Preparation of Eynone 14

Structure Shown in FIG. 3

To a solution of the Weinreb amide 13 (3.03 g, 9.58 mmol) in dry THF (20 ml), a solution of ethynyl magnesium bromide (0.5 M, 30.0 ml, 15 mmol) in THF was added in drops and stirred at room temperature for 4 h. The reaction mixture was then poured over ice cold 0.5 M aqueous HCl, followed by the addition of methylen chloride (150 ml). The organic layer was separated and washed with water and brine. The product was purified by chromatography on a column of silica gel using ethylacetate-hexane (3:8) as eluant. The weight of the product was 1.81 g. $^1$H-NMR (CDCl$_3$): 5.69 (d, J=4.9 Hz, H-1), 4.75 (dd, J=1.9, 7.6 Hz, H-3), 4.69 (dd, J=2.7, 7.6 Hz, H-4), 4.40 (m, H-2, H-5), 3.38 (s, C$\underline{H}$), 1.53, 1.46, 1.35, and 1.34 (4×s, isopropylidene methyls).

Figure 4:
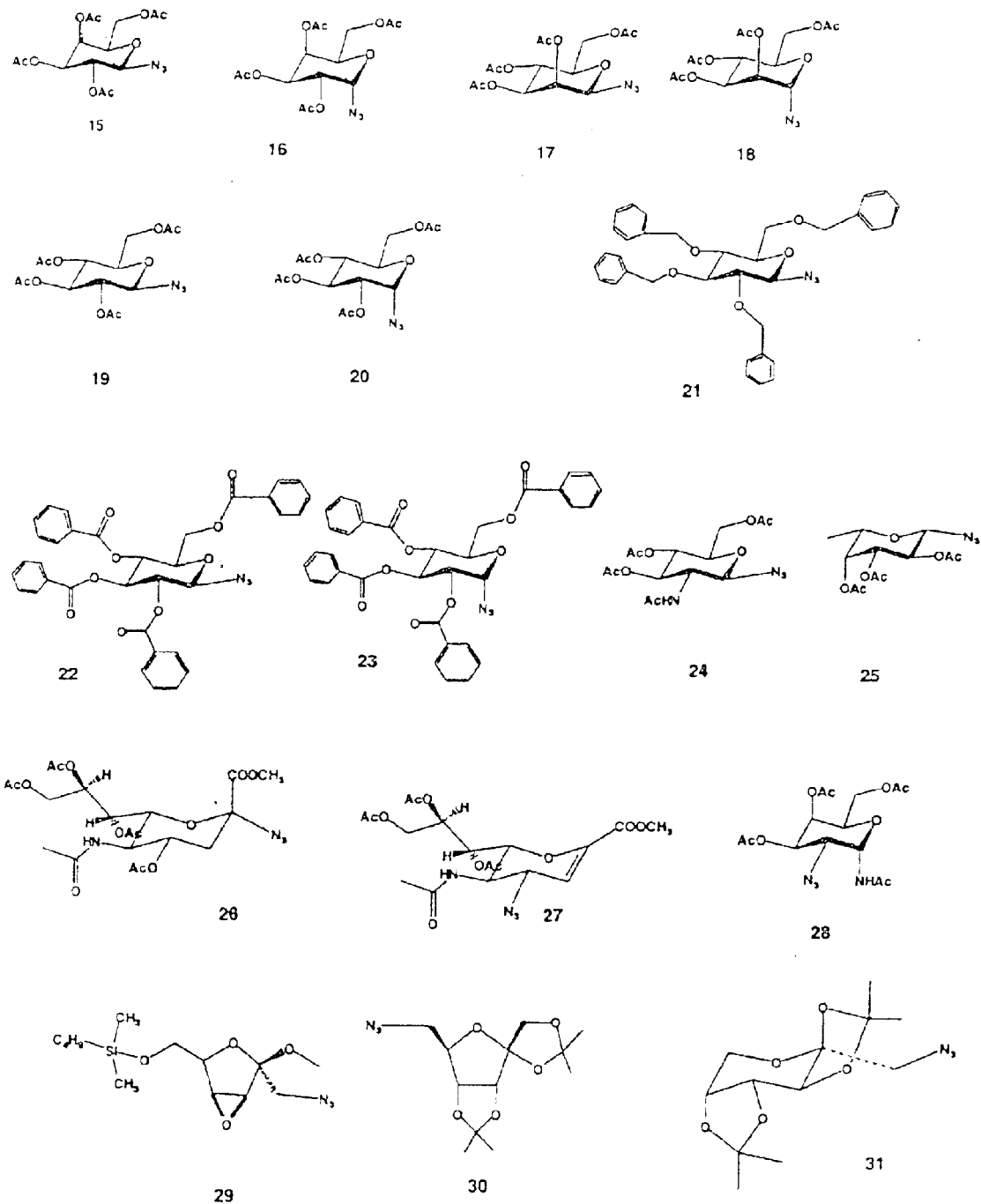
FIG. 4 presents structures of intermediate azido compounds 15–31.

Azides 15–31 Shown in FIG. 4

The preparation of the azides structures 15–26 are disclosed in earlier patents, incorporated by reference; (S. Sabesan, U.S. Pat. No. 5,288,859 (1994); S. Sabesan, U.S. Pat. No. 5,674,988 (1997); S. Sabesan, U.S. Pat. No. 5,756, 712, (1998). Compounds 27–29 are prepared by similar methods.

Preparation of Azide 30

Compound 4 (11.7 g, 45 mmol) was dissolved in methylene chloride (enough volume to freely dissolve the starting material) containing pyridine (4.3 g) and cooled to 0° C. Trifluromethanesulfonic anhydride (15.2 g) was added in drops to the above solution maintained under dry nitrogen atmosphere. Following addition, the reaction mixture was stirred for 60 min, then diluted with methylene chloride and washed with ice-cold water,). 5 M hydrochloric acid solution, and saturated aqueous sodium bicarbonate solution. The organic solvent was dried and concentrated to dryness. This product was dissolved in anhydrous N,N-dimethylformamide containing sodium azide (29 g) and was heated to 60° C. under nitrogen atmosphere overnight. It was then concentrated, the residue dissolved in methylene chloride-water and washed with water and brine. It was then dried and concentrated. The product was purified by chromatography on a column of silica gel using ethylacetate-hexane (1:8) as eluant. The weight of the product was 7.54 g. NMR (CDCl$_3$) δ: 4.65 (dd, J=1.3, 5.7 Hz, H-4), 4.61 (d, J=5.7 Hz, H-3), 4.33 (d, J=10.1 Hz, H-1a), 4.20 (dt, J=1.3, 7.1 Hz, H-5), 4.06 (d, J=10.1 Hz, H-1b), 3.53 (dd, J=7.8, 12.6 Hz, H-6a), 3.30 (dd, J=6.3, 13.0 Hz, H-6b), 1.48, 1.45, 1.39, 1.32 (4×s, isopropylidene methyls).

Preparation of Azide 31

Alcohol 3 (13 g) was converted to the azide 31 as described above for compound 30. After chromatographic purification on silica gel using ethyl acetate-hexane (1:7), pure 31 was obtained as a colorless crystals (11.0 g). $^1$H-NMR (CDCl$_3$) δ: 4.61 (dd, J=2.5, 7.7 Hz, H-4), 4.29 (d, J=2.5 Hz, H-5), 4.24 (dd, J=6.9 Hz, H-3), 3.92 (dd, J=1.9, 13.2 Hz, H-6a), 3.77 (dd, J=13.2 Hz, H-6b), 3.59 (d, J=12.6 Hz, H-1a), 3.28 (d, J=13.2 Hz, H-1b), 1.56, 1.49, 1.47, 1.35 (4×s, isopropylidene methyls).

EXAMPLES

Example 1

Cycloaddition from the Azide 31 and the Acetylene 14 to give Products 32a & 32b

Figure 5:
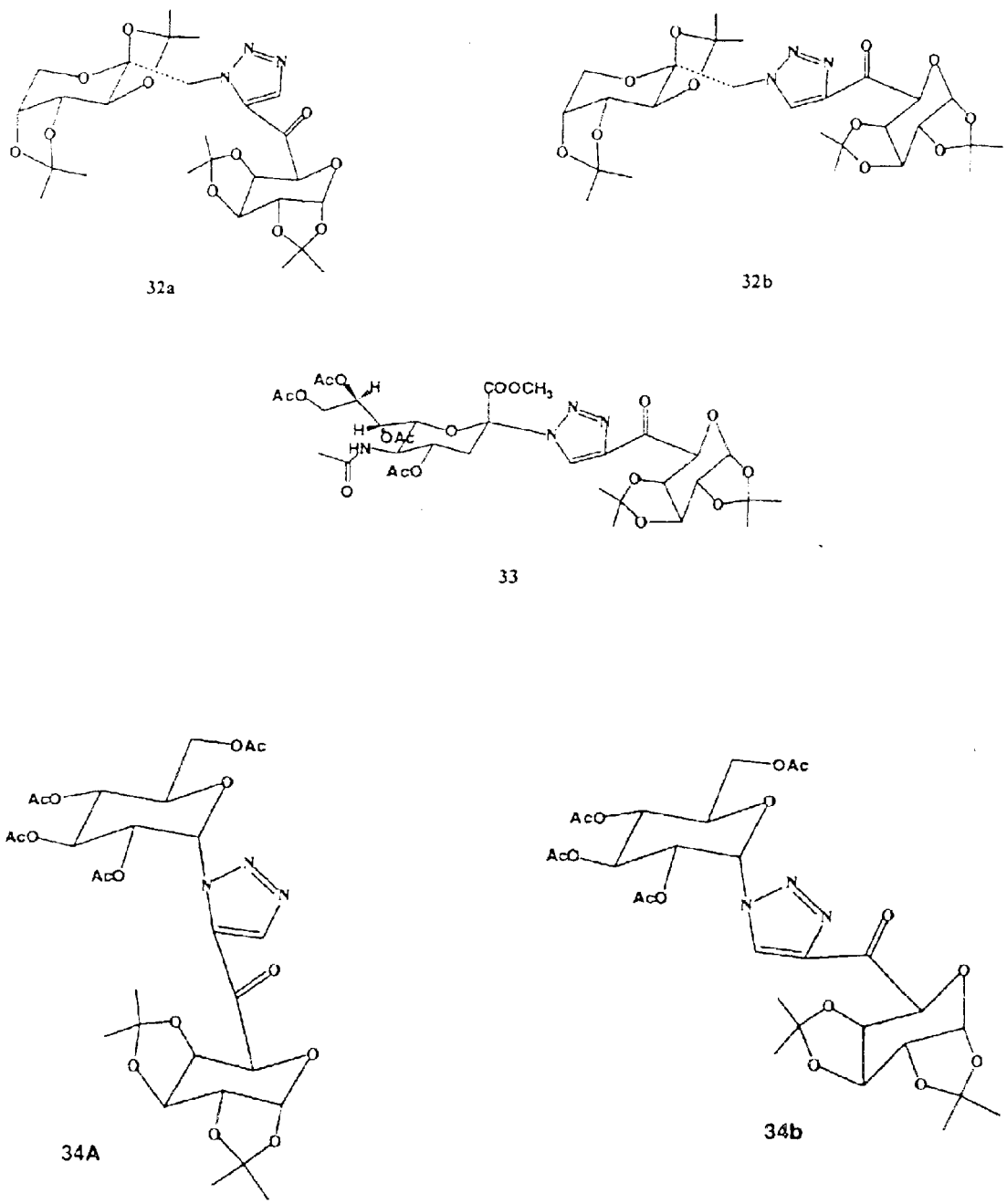
FIG. 5 represents structures of inventive compounds 32a and 32b, 33 and 34a and 34b.

Structures Shown in FIG. 5

Azide 31 (112 mg, 0.39 mmol) and the acetylene 14 (112 mg, 0.40 mmol) in toluene (1 ml) was heated to 110° C. for 20 h. The reaction mixture was cooled and the major product was isolated by chromatography on a column of silica gel using etyl acetate-hexane as eluant. After elution of the minor product 32a, the major component 32b eluted out. The weight of 32b was 161 mg.

$^1$H-NMR (CDCl$_3$): 32a: 8.32 (s), 5.68 (d, H-1), 5.43 (d, H-1'a), 4.91 (d, H-1'b), 4.67 (m, H-3), 4.66 (m, H-4), 4.63 (m, H-2), 4.59 (broad s, H-5), 4.47 (d, H-3'), 4.37 (d, H-5'), 4.18 (broad d, H-4'), 3.88 and 3.76 (dd, H-6a and H-6b), 1.6–1.2 and 0.57 (8×s, isopropylidene methyls).

$^1$H-NMR (CDCl$_3$): 32b: 8.36 (s), 5.75 (d, H-1), 5.37 (d), 5.04 (dd), 4.73 (d, H-1'a), 4.71–4.64 (m, H-3 and H-4), 4.60 (d, H-1'b), 4.43 (m, H-2), 4.41 (d, H-5), 4.23 (dd, H-5'), 3.87 and 3.76 (d, H-6'a and H-6'b), 1.6–1.1 and 0.85 (8×s, isopropylidene methyls).

Example 2

Cycloaddition from the Azide 27 and the Acetylene 14 to give Product 33

Structure Shown in FIG. 5

Azide 26 (205 mg, 0.40 mmol) and the acetylene 14 (112 mg, 0.40 mmol) in toluene (1 ml) was heated to 100° C. for 36 h. The reaction mixture was cooled and the major product was isolated by chromatography on a column of silica gel using etyl acetate-hexane-ethanol=10:10:1 as eluant. The weight of the product was 162 mg. $^1$H-NMR (CDCl$_3$): 8.69 (s), 5.83 (d, J=4.9 Hz, H-1), 5.47 (m, H-8'), 5.36 (dd, J=1.9, 8.7 Hz, H-7'), 5.32 (d, J=9.8 Hz, NH), 5.25 (m, H-4'), 5.21 (d, J=1.9 Hz, H-5), 5.01 (dd, 1.9, 7.6 Hz, H-4), 4.73 (dd, J=3.0, 7.9 Hz, H-3), 4.45 (dd, J=2.7, 5.3 Hz, H-2), 4.38 (dd, J=2.3, 11.0 Hz, H-6), 4.27 (dd, J=3.0, 12.5 Hz, H-9'a), 4.12 (dd, J=4.9, 12.0 Hz, H-9'b), 4.04 (t, J=10.6 Hz, H-5'), 3.82 (s, COOCH$_3$), 3.48 (dd, J=4.5, 12.9 Hz, H-3'eq), 2.63 (dd, J=11.7, 13.2 Hz, H-3'ax), 2.16, 2.12, 2.07, 2.06, 1.93 (5×s, CHZ$_3$CO), 1.57, 1.43, 1.37, 1.28 (4×s, isopropylidene methyls).

Example 3

Cycloaddition from the Azide 20 and the Acetylene 14 to give Products 34a (Minor) and 34b (Major)

Structures Shown in FIG. 5

Azide 20 (186 mg, 0.50 mmol) and the acetylene 14 (141 mg, 0.50 mmol) in toluene (1 ml) was heated to 100° C. for 72 h. The reaction mixture was cooled and the major product was isolated by chromatography on a column of silica gel using ethyl acetate-hexane=1:1 as eluant. The weight of the major product 34b was 224 mg and the minor product 34a was 31 mg.

$^1$H-NMR (CDCl$_3$): 34a: 8.51 (s), 7.12 (d, J=6.0 Hz), 6.18 (t, J=9.5 Hz, H-3'), 5.71 (d, J=4.7 Hz, H-1), 5.45 (dd, J=6.0, 10.1 Hz, H-2'), 5.29 (dd, J=9.5, 10.4 Hz, H-4'), 4.68 (dd, J=2.2, 6.9 Hz, H-3), 4.61 (m, H-4, H-5), 4.41 (m, H-5', H-2), 4.24 (dd, J=3.5, 12.3 Hz, H-6'a), 3.99 (dd, J=2.2, 12.6 Hz, H-6'b), 2.06, 2.04, 2.00, 1.84 (4×s, OCOCH$_3$), 1.53, 1.36, 1.35, 1.28 (4×s, isopropylidene methyls).

$^1$H-NMR (CDCl$_3$): 34b: 8.33 (s), 6.42 (d, J=6.0 Hz, H-1'), 6.23 (t, J=9.5 Hz, H-3'), 5.76 (d, J=4.7 Hz, H-1), 5.35 (dd, J=6.0, 10.1 Hz, H-2'), 5.36 (d, J=2.2 Hz, H-5), 5.26 (dd, J=9.5, 10.1 Hz, H-4'), 5.08 (dd, J=2.5, 7.9 Hz, H-4), 4.74 (dd, J=2.8, 7.9 Hz, H-3), 4.46 (dd, J=2.8, 5.1 Hz, H-2), 4.32 (m, H-5'), 4.26 (dd, J=4.4, 12.6 Hz, H-6'a), 4.03 (dd, J=2.2, 12.9 Hz, H-6'b), 2.07, 2.06, 2.04, 1.87 (4×s, CH$_3$CO), 1.59, 1.41, 1.37, 1.26 (isopropylidene methyls).

Example 4

Combinatorial Parallel Synthesis of Triazolyl Glycosides

Figure 6:
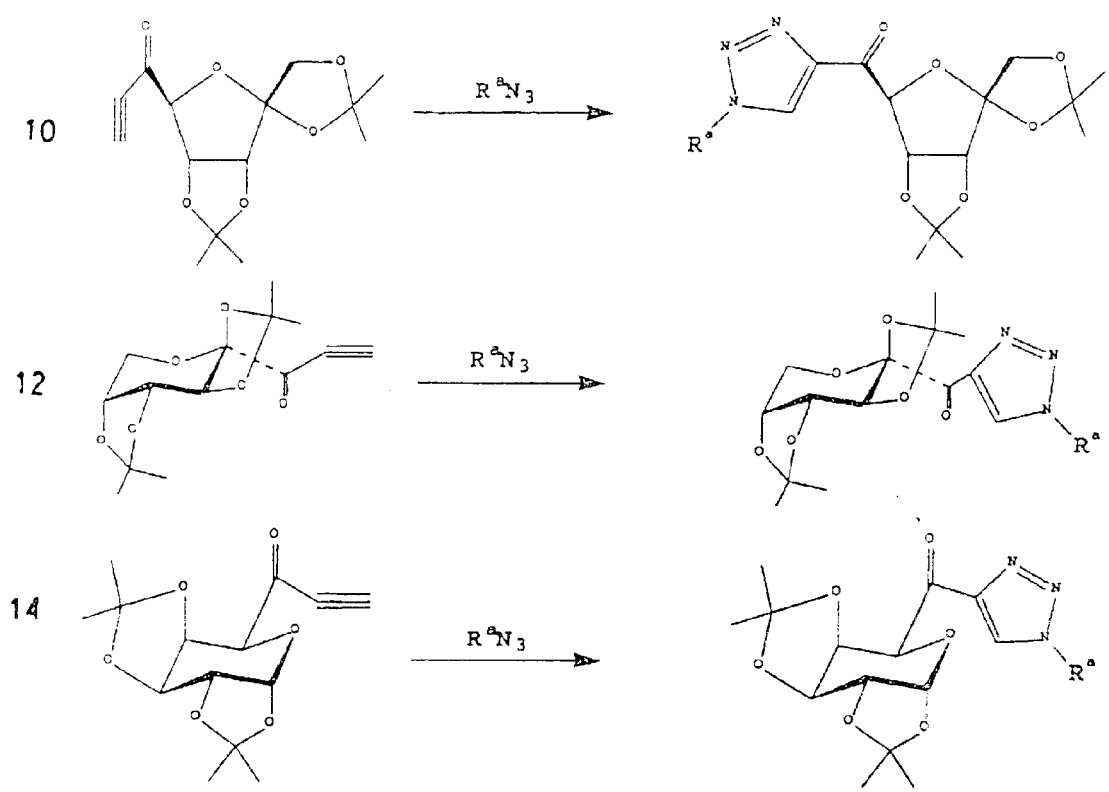
FIG. 6 is a representation of the synthetic conversions used to generate the libraries of compounds in Tables 1, 2 and 3.

The acetylenes 10, 12, and 14 (0.25 mmol) were reacted with a series of azidosugars (0.25 mmol). The conversions are shown in FIG. 6, wherein R$^a$ represents the non azide portion of various members of the group of azide compounds 15–30. The libraries of triazoles were obtained by concentration of the reaction products. The identities of the crude products were established either by Mass Spectroscopy or proton NMR Spectroscopy. Tables 1, 2 and 3 list the starting materials which gave products according to the conversions shown in FIG. 6, from acetylenes 10, 12, and 14, respectively.

TABLE 1

| Azido Sugar | Acetylene 10 | Product Weight |
| --- | --- | --- |
| 15 (93 mg) | 70 mg | 151 mg |
| 16 (93 mg) | 70 mg | 177 mg |
| 17 (93 mg) | 70 mg | 75 mg |
| 18 (93 mg) | 70 mg | 158 mg |
| 19 (93 mg) | 70 mg | 151 mg |
| 21 (141 mg) | 70 mg | 94 mg |
| 22 (141 mg) | 70 mg | 225 mg |
| 23 (127 mg) | 70 mg | 111 mg |
| 24 (93 mg) | 70 mg | 163 mg |

TABLE 1-continued

| Azido Sugar | Acetylene 10 | Product Weight |
|---|---|---|
| 25 (79 mg) | 70 mg | 159 mg |
| 26 (129 mg) | 70 mg | 111 mg |
| 27 (99 mg) | 70 mg | 148 mg |
| 28 (93 mg) | 70 mg | 107 mg |
| 29 (79 mg) | 70 mg | 128 mg |
| 30 (71 mg) | 70 mg | 129 mg |

TABLE 2

| Azido Sugar | Acetylene 12 | Product Weight |
|---|---|---|
| 15 (93 mg) | 70 mg | 129 mg |
| 16 (93 mg) | 70 mg | 148 mg |
| 18 (93 mg) | 70 mg | 186 mg |
| 19 (93 mg) | 70 mg | 170 mg |
| 22 (141 mg) | 70 mg | 210 mg |
| 24 (93 mg) | 70 mg | 160 mg |
| 25 (79 mg) | 70 mg | 158 mg |
| 27 (99 mg) | 70 mg | 260 mg |
| 28 (93 mg) | 70 mg | 115 mg |
| 29 (79 mg) | 70 mg | 120 mg |
| 30 (71 mg) | 70 mg | 128 mg |

TABLE 3

| Azido Sugar | Acetylene 14 | Product Weight |
|---|---|---|
| 15 (93 mg) | 70 mg | 146 mg |
| 16 (93 mg) | 70 mg | 154 mg |
| 17 (93 mg) | 70 mg | 158 mg |
| 19 (93 mg) | 70 mg | 69 mg |
| 21 (141 mg) | 70 mg | 184 mg |
| 22 (141 mg) | 70 mg | 145 mg |
| 23 (127 mg) | 70 mg | 149 mg |
| 24 (93 mg) | 70 mg | 155 mg |
| 25 (79 mg) | 70 mg | 104 mg |
| 27 (99 mg) | 70 mg | 107 mg |
| 28 (93 mg) | 70 mg | 170 mg |
| 29 (79 mg) | 70 mg | 125 mg |
| 30 (71 mg) | 70 mg | 131 mg |

What is claimed is:

1. A process for the preparation of a compound having the structure I,

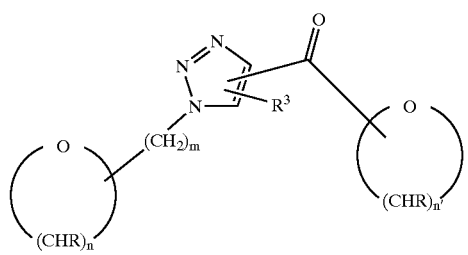

I wherein each R, independently, is selected from the group consisting of hydrogen, hydroxy, alkoxy having up to 8 carbon atoms, acyloxy having up to 8 carbon atoms, acylamino having up to 8 carbon atoms, $C_1$ to $C_{20}$ hydrocarbyl and substituted hydrocarbyl and amino; $R^3$ is selected from the group consisting of H, $C_1$ to $C_{20}$ hydrocarbyl and substituted hydrocarbyl; m is 0 or 1, and n and n' are, independently, 4 or 5, comprising: contacting azides of the structure IA:

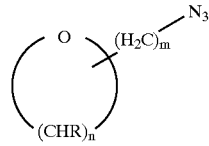

IA wherein R is selected from the group consisting of hydrogen, hydroxy, alkoxy having up to 8 carbon atoms, acyloxy having up to 8 carbon atoms, acylamino having up to 8 carbon atoms, $C_1$ to $C_{20}$ hydrocarbyl or substituted hydrocarbyl and amino; n is 4 or 5, and m is 0 or 1,
with compounds of the structure IB

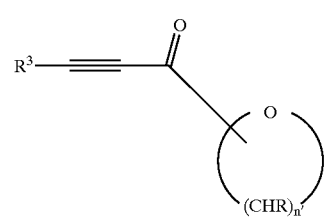

IB wherein R is as described above and $R^3$ is selected from the group consisting of H, $C_1$ to $C_{20}$ hydrocarbyl and substituted hydrocarbyl; and n' is 4 or 5.

2. A process according to claim 1 for the preparation of triazolyldisaccharides of the structure II,
wherein $R^1$ is selected from the group consisting of H, Na, $C_1$–$C_{20}$ alkyl,
wherein $R^2$ is selected from the group consisting of hydroxy,

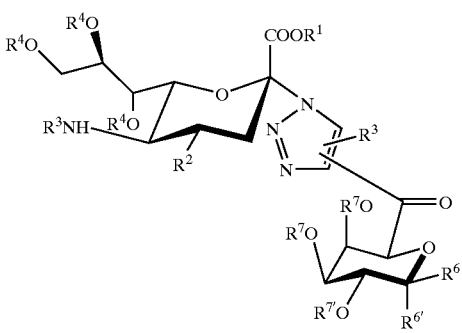

II alkoxy having from 1 to 8 carbon atoms, acyloxy having from 1 to 8 carbon atoms, acylamino having from 1 to 8 carbon atoms, amino, hydrogen, and guanidino;
wherein $R^3$ is selected from the group consisting of H, $C_1$ to $C_{20}$ hydrocarbyl, and substituted hydrocarbyl;
wherein $R^4$ is selected from the group consisting of H, acyl having from 1 to 8 carbon atoms, and alkyl having 1 to 20 carbon atoms;
wherein $R^6$ and $R^{6'}$ are selected from the group consisting of H, OH, $C_1$ to $C_{20}$ alkoxy, $C_1$ to $C_{20}$ substituted alkoxy, mono-, di- or oligosaccharide, and alkylideneoxy taken together with $R^{7'}$ when $R^{7'}$ is not H, provided that one of $R^6$ and $R^{6'}$ must be H but $R^6$ and $R^{6'}$ may not both be H; and
$R^7$ and $R^{7'}$ are selected from the group consisting of H, acyl having from 1 to 8 carbon atoms, $C_1$ to $C_{20}$ alkyl, aryl, and alkylidene taken together with an adjacent $R^6$, $R^{6'}$, $R^7$ and $R^{7'}$;

comprising contacting compounds of the structure IIA:

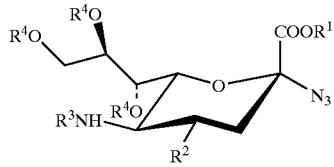

IIA wherein $R^1$ is selected from the group consisting of H, Na, and $C_1$–$C_{20}$ alkyl, $R^2$ is selected from the group consisting of hydroxy, alkoxy having from 1 to 8 carbon atoms, acyloxy having from 1 to 8 carbon atoms, acylamino having from 1 to 8 carbon atoms, amino, hydrogen, and guanidino;

$R^3$ is selected from the group consisting of H, $C_1$ to $C_{20}$ hydrocarbyl and substituted hydrocarbyl; and $R^4$ is selected from the group consisting of H, acyl having from 1 to 8 carbon atoms and alkyl having 1 to 20 carbon atoms;

with compounds of the structure IIB

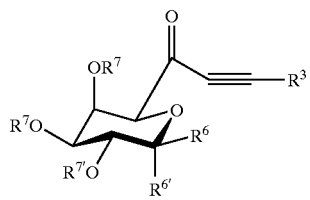

IIB wherein $R^3$ is selected from the group consisting of H, $C_1$ to $C_{20}$ hydrocarbyl and substituted hydrocarbyl;

$R^6$ and $R^{6'}$ are selected from the group consisting of H, OH, $C_1$ to $C_{20}$ alkoxy and substituted alkoxy, mono-, di- or oligosaccharide, and alkylideneoxy taken together with $R^{7'}$ when $R^{7'}$ is not H, provided that one of $R^6$ and $R^{6'}$ must be H but $R^6$ and $R^{6'}$ may not both be H; and $R^7$ and $R^{7'}$ are selected from the group consisting of H, acyl having from 1 to 8 carbon atoms, $C_1$ to $C_{20}$ alkyl, aryl, and alkylidene taken together with an adjacent $R^6$, $R^{6'}$, $R^7$ and $R^{7'}$.

3. A process according to claim 1 for the preparation of a compound of the structure III, wherein $R^3$ is selected from the group consisting of H, $C_1$ to $C_{20}$ hydrocarbyl, and $C_1$ to $C_{20}$ substituted hydrocarbyl;

wherein $R^8$ is selected from the group consisting of H, alkyl having from 1 to 20 carbon atoms, and acyl having from 1 to 8 carbon

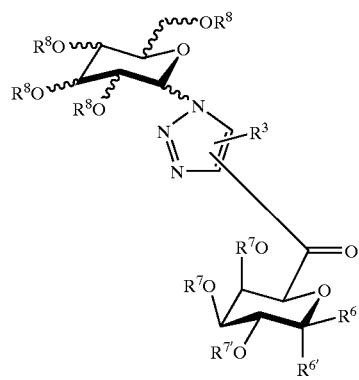

III atoms;

wherein $R^6$ and $R^{6'}$ are selected from the group consisting of H, OH, $C_1$ to $C_{20}$ alkoxy, $C_1$ to $C_{20}$ substituted alkoxy, mono-, di- or oligosaccharide, and alkylideneoxy taken together with $R^{7'}$, when $R^{7'}$ is not H, provided that one of $R^6$ and $R^{6'}$ must be H but $R^6$ and $R^{6'}$ may not both be H; and wherein $R^7$ and $R^{7'}$ are selected from the group consisting of H, acyl having from 1 to 8 carbon atoms, $C_1$ to $C_{20}$ alkyl, aryl, and alkylidene taken together with an adjacent $R^6$, $R^{6'}$, $R^7$ or $R^{7'}$, comprising: contacting a compound of the structure IIIA:

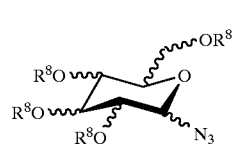

IIIA wherein $R^8$ is selected from the group consisting of H, alkyl, wherein the alkyl having from 1 to 20 carbon atoms, and acyl, where the acyl group contains from 1 to 8 carbon atoms;

with compounds of the structure IIB,

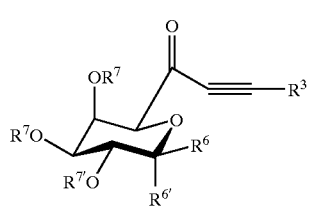

IIB wherein $R^3$ is selected from the group consisting of H $C_1$ to $C_{20}$ hydrocarbyl and substituted hydrocarbyl;

$R^6$ and $R^{6'}$ are selected from the group consisting of H, OH, $C_1$ to $C_{20}$ alkoxy and substituted alkoxy, mono-, di- or oligosaccharide, and alkylideneoxy taken together with $R^{7'}$ when $R^{7'}$ is not H, provided that one of $R^6$ and $R^{6'}$ must be H but $R^6$ and $R^{6'}$ may not both be H; and $R^7$ and $R^{7'}$ are selected from the group consisting of H, acyl having from 1 to 8 carbon atoms, $C_1$ to $C_{20}$ alkyl, aryl, and alkylidene taken together with an adjacent $R^6$, $R^{6'}$, $R^7$ and $R^{7'}$.

4. Acetylenic compounds of the structure IB

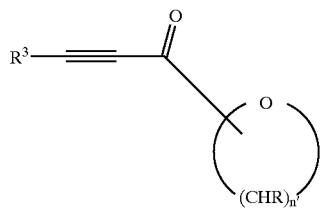

IB wherein R is selected from the group consisting of hydrogen, hydroxy, alkoxy having up to 8 carbon atoms, acyloxy having up to 8 carbon atoms, acylamino having up to 8 carbon atoms, $C_1$ to $C_{20}$ hydrocarbyl, substituted hydrocarbyl and amino; $R^3$ is selected from the group consisting of H, $C_1$ to $C_{20}$ hydrocarbyl and substituted hydrocarbyl; and n' is 5.

5. Acetylenic compounds according to claim 4 of the structure IIB

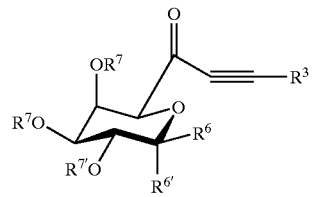

IIB wherein $R^3$ is selected from the group consisting of H, $C_1$ to $C_{20}$ hydrocarbyl and substituted hydrocarbyl;

$R^6$ and $R^{6'}$ are selected from the group consisting of H, OH, $C_1$ to $C_{20}$ alkoxy and substituted alkoxy, mono-, di- or oligosaccharide, and alkylideneoxy taken together with $R^{7'}$ when $R^{7'}$ is not H, provided that one of $R^6$ and $R^{6'}$ must be H but $R^6$ and $R^{6'}$ may not both be H; and $R^7$ and $R^{7'}$ are selected from the group consisting of H, acyl having from 1 to 8 carbon atoms, $C_1$ to $C_{20}$ alkyl, aryl, and alkylidene taken together with an adjacent $R^6$, $R^{6'}$, $R^7$ and $R^{7'}$.

* * * * *